(12) United States Patent
Kajii

(10) Patent No.: US 9,220,878 B2
(45) Date of Patent: Dec. 29, 2015

(54) AUXILIARY DILATOR AND CATHETER ASSEMBLY HAVING THE SAME

(75) Inventor: Tatsuhiko Kajii, Seto (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 0 days.

(21) Appl. No.: 13/190,207

(22) Filed: Jul. 25, 2011

(65) Prior Publication Data

US 2012/0109109 A1 May 3, 2012

(30) Foreign Application Priority Data

Oct. 29, 2010 (JP) .................................. 2010-243823

(51) Int. Cl.
*A61M 29/00* (2006.01)
*A61M 25/06* (2006.01)

(52) U.S. Cl.
CPC ........... *A61M 29/00* (2013.01); *A61M 25/0662* (2013.01); *A61M 25/0668* (2013.01); *A61M 2025/0681* (2013.01); *A61M 2025/0687* (2013.01)

(58) Field of Classification Search
CPC ...................... A61M 25/0668; A61M 25/0662; A61M 2025/0681; A61M 2025/0687; A61M 29/00; A61M 2029/025; A61M 2025/0024; A61M 2025/018–2025/0188; A61B 1/32
USPC .............................. 604/104–109, 161, 164.01, 604/164.09–164.1, 164.12, 170.02, 528, 604/509
See application file for complete search history.

(56) References Cited

U.S. PATENT DOCUMENTS

| | | | |
|---|---|---|---|
| 4,345,606 A | | 8/1982 | Littleford |
| 4,473,067 A | | 9/1984 | Schiff |
| 5,125,904 A | | 6/1992 | Lee |
| 5,158,545 A | * | 10/1992 | Trudell et al. .................. 604/509 |
| 5,221,263 A | * | 6/1993 | Sinko et al. .................... 604/161 |
| 5,454,790 A | * | 10/1995 | Dubrul .......................... 604/104 |
| 5,902,282 A | * | 5/1999 | Balbierz ........................ 604/264 |
| 6,206,871 B1 | * | 3/2001 | Zanon et al. ............... 604/891.1 |
| 8,608,702 B2 | | 12/2013 | Beal et al. |

(Continued)

FOREIGN PATENT DOCUMENTS

EP 0 631 793 A1 1/1995
JP Y2-08-007869 1/1991

(Continued)

OTHER PUBLICATIONS

Nov. 21, 2011 European Search Report issued in European Patent Application No. 11173681.5.

(Continued)

*Primary Examiner* — Bhisma Mehta
*Assistant Examiner* — Larry R Wilson
(74) *Attorney, Agent, or Firm* — Oliff PLC

(57) ABSTRACT

An object of the present invention is to provide a device used in an operation using a catheter assembly and the catheter assembly having the device, which allows a hole formed in a body surface to have a minimum size and a catheter to be smoothly inserted into the body. An auxiliary dilator includes a body part having a tapered portion tapering toward a front end of the auxiliary dilator. The body part surrounds an extension part of a main dilator with a front end entry portion of the extension part protruding from the tapered portion, and a separation part attached to the body part enabling the body part to be removed from the main dilator.

2 Claims, 9 Drawing Sheets

(56) References Cited

U.S. PATENT DOCUMENTS

| | | | |
|---|---|---|---|
| 2002/0087076 A1 | 7/2002 | Meguro et al. | |
| 2004/0092879 A1* | 5/2004 | Kraus et al. | 604/158 |
| 2006/0064056 A1 | 3/2006 | Coyle et al. | |
| 2007/0185446 A1* | 8/2007 | Accisano, III | 604/104 |
| 2009/0105652 A1 | 4/2009 | Beal et al. | |

FOREIGN PATENT DOCUMENTS

| | | |
|---|---|---|
| JP | A-07-051381 | 2/1995 |
| JP | A-09-225035 | 9/1997 |
| JP | A-2002-143318 | 5/2002 |
| JP | A-2002-143319 | 5/2002 |
| JP | A-2010-207388 | 9/2010 |
| WO | WO 2009/052327 A1 | 4/2009 |

OTHER PUBLICATIONS

European Office Action dated Feb. 21, 2013 for European Application No. 11 173 681.5.

Dec. 17, 2013 Office Action issued in European Patent Application No. 11 173 681.5.

Chinese Office Action issued in Chinese Patent Application No. 201110218291.8 dated Feb. 8, 2014 (w/ translation).

Nov. 12, 2013 Office Action issued in Japanese Patent Application No. 2012-246633 (with translation).

Aug. 20, 2014 Office Action issued in Chinese Application No. 201110218291.8 (with English translation).

* cited by examiner

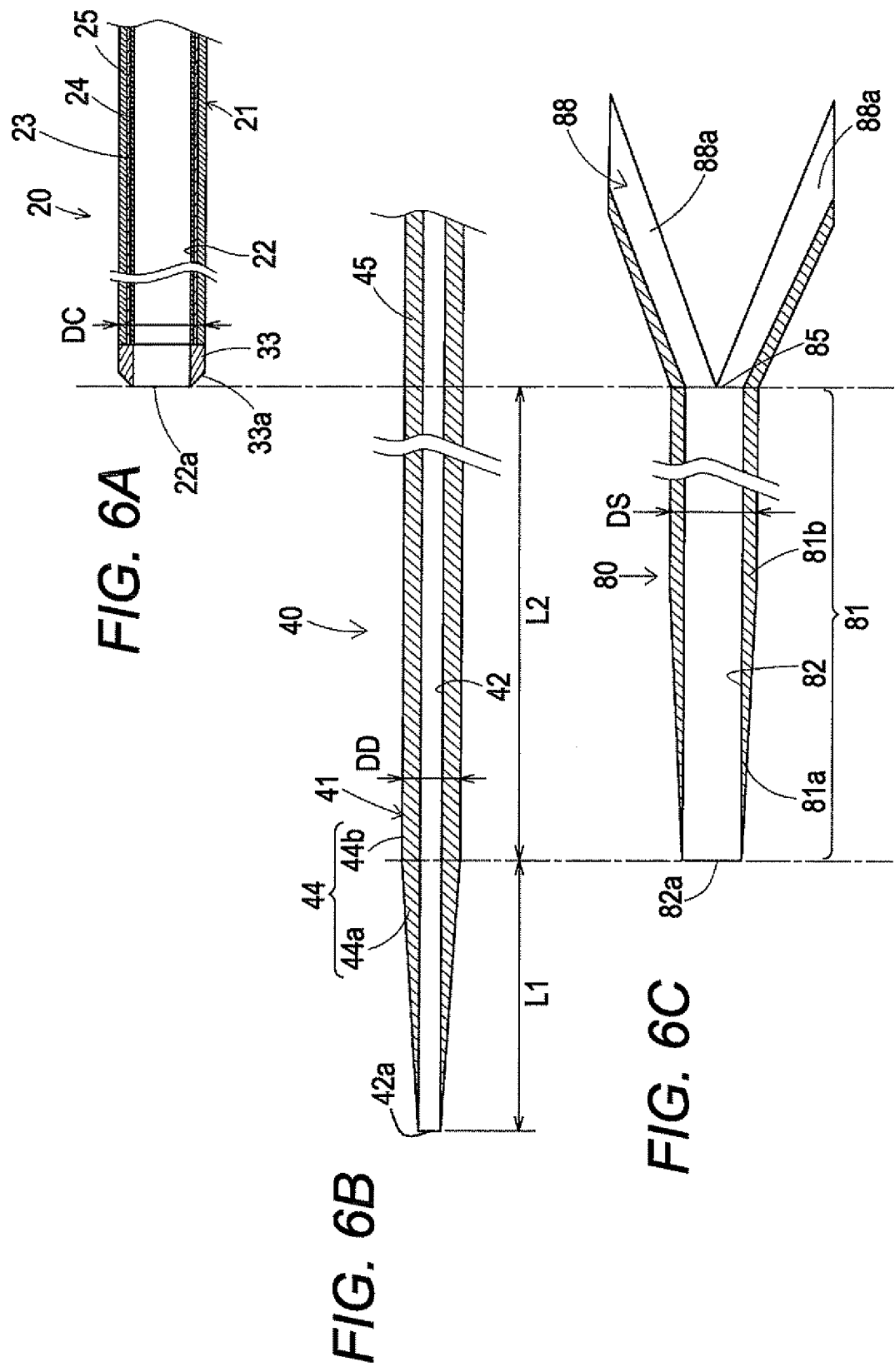

AUXILIARY DILATOR AND CATHETER ASSEMBLY HAVING THE SAME

CROSS REFERENCE TO RELATED APPLICATIONS

This application is based on Japanese Patent Application No. 2010-243823 filed with the Japan Patent Office on Oct. 29, 2010, the entire content of which is hereby incorporated by reference.

TECHNICAL FIELD

The present invention relates to an auxiliary dilator used in a catheter assembly having a dilator and a catheter, and a catheter assembly having the auxiliary dilator.

BACKGROUND ART

Conventionally, an assistive device called a sheath, into which a catheter used for diagnosis and treatment is inserted, is used to insert the catheter into a vessel or the like (see, for example, JP-A-9-225035, JP-Y-8-7869, and JP-A-7-51381). The sheath is inserted into a vessel in advance before the catheter is inserted into the vessel. The catheter is then introduced into the vessel by being inserted into the sheath.

In such an operation, as large a hole as an outer diameter of the sheath needs to be bored in the vessel. This operation therefore has some undesirable effects. For example, the operation is not suitable for insertion of the catheter through a relatively thin vessel (such as a radial artery in a wrist region), and the patient suffers pain during the operation.

Recently, therefore, there has been proposed a catheter assembly enabling a catheter to be inserted into a vessel without using a sheath (see, for example, JP-A-2002-143318 and JP-A-2002-143319). Such a catheter assembly has a catheter for diagnosis/treatment (hereinafter simply referred to as "catheter") such as a guiding catheter used for diagnosis or treatment inside a body, and a dilator to be inserted into the catheter. The dilator has a dilation portion which protrudes from a front end of the catheter and enters a vessel. In the catheter assembly having the above configuration, the dilation portion of the dilator is first to enter the vessel. Then, the catheter is inserted into the vessel together with the dilator. After the catheter assembly is inserted by a predetermined length into a body, only the dilator is pulled out of the body to be removed leaving the catheter behind.

SUMMARY OF INVENTION

For such a catheter assembly, a hole needs to be bored in the body surface into a vessel inside the body so as to insert the dilator into the vessel. The hole to be bored is minuter than that bored for the operation using the conventional sheath. Such a catheter assembly is thus very useful for the operation. However, since the dilator of the catheter assembly is inserted into the catheter, the maximum outer diameter of the dilation portion of the dilator is inevitably smaller than that of the catheter. Accordingly, the hole bored so as to insert the dilator into the vessel has an outer diameter that is substantially equal to the maximum outer diameter of the dilation portion of the dilator and a little smaller than the outer diameter of the catheter. As a result, there is a difference between the maximum outer diameter of the dilation portion of the dilator extending from the front end of the catheter and the outer diameter of the front end of the catheter. The diameter of the hole bored in the body surface is smaller than the outer diameter of the catheter by this difference.

This difference causes a stepped portion between the front end portion of the catheter and the peripheral surface of the dilation portion of the dilator protruding from the front end of the catheter. The stepped portion may make it difficult for an operator such as a physician to insert the catheter smoothly into the body.

In the operation using the sheath or the like, on the other hand, there are various disadvantages as described above in boring a hole, which is sufficient to insert the catheter, in the body surface into a vessel.

The present invention has been made in view of the foregoing circumstances. An object of the present invention is to provide a device that is used for an operation using a catheter assembly and that can insert a catheter into a body more smoothly while allowing the size of a hole formed in a body surface to be minimum, and a catheter assembly that includes the device.

The above-described object of the invention is achieved by the following structures.

<1> A first aspect of the present invention is an auxiliary dilator configured to attached to a main dilator to be inserted into a catheter and having an extension part extending from a front end of the catheter, including: a body part having a tapered portion tapering toward a front end of the auxiliary dilator and surrounding the extension part with a front end portion of the extension part of the main dilator protruding from the tapered portion; and a separation part attached to the body part enabling the body part to be removed from the main dilator.

BRIEF DESCRIPTION OF DRAWINGS

The foregoing and other objects, features, aspects and advantages of the invention will become more apparent from the following detailed description when taken in conjunction with the accompanying drawings.

FIGS. 6A, 6B and 6C are views illustrating configurations of the catheter, the main dilator and the auxiliary dilator, respectively, according to the first embodiment and positional relationships between these components.

DESCRIPTION OF EMBODIMENTS

Figure 1:
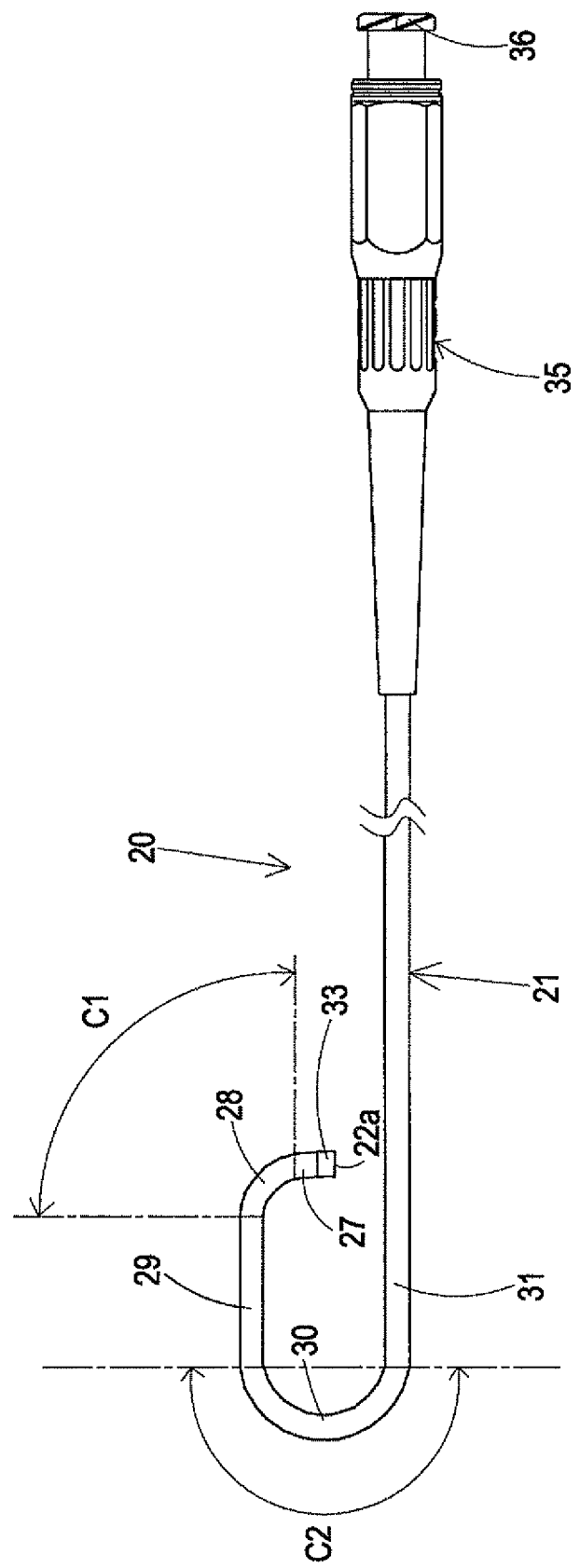
FIG. 1 is a view illustrating an entire catheter of a catheter assembly according to a first embodiment.

Preferred embodiments of the present invention will be described below with reference to the accompanying drawings, in which like reference characters designate similar or identical parts throughout the several views thereof.

<1> The first aspect of the present invention is an auxiliary dilator configured to attached to a main dilator to be inserted into a catheter and having an extension part extending from a front end of the catheter, including: a body part having a tapered portion tapering toward a front end of the auxiliary dilator and surrounding the extension part with a front end portion of the extension part of the main dilator protruding from the tapered portion; and a separation part attached to the body part enabling the body part to be removed from the main dilator.

<2> A second aspect of the present invention is the auxiliary dilator according to the first aspect, wherein the separation part has a pair of small pieces attached to a rear end portion of the body part.

<3> A catheter assembly according to a third aspect of the present invention includes: the auxiliary dilator according to the first or second aspect; the catheter; and the main dilator.

<4> A fourth aspect of the present invention is the catheter assembly according to the third aspect, wherein the front end portion of the extension part of the main dilator has a tapered shape tapering toward a front end of the main dilator, the front end portion of the extension part of the main dilator has a taper angle substantially equal to a taper angle of the tapered portion of the auxiliary dilator, and a tapered inclined surface of the front end portion of the extension part of the main dilator and a tapered inclined surface of the tapered portion of the auxiliary dilator are substantially in alignment with each other when the body part of the auxiliary dilator surrounds the extension part of the main dilator.

<1> The auxiliary dilator according to the first aspect of the present invention is attached to the extension part of the main dilator. Accordingly, a hole formed in the body surface into a vessel or the like and enlarged by the main dilator can be further enlarged by the tapered portion of the auxiliary dilator. In addition, it is possible to avoid formation of a hole that is unnecessarily larger than the outer diameter of the catheter. Therefore, the size of the hole formed in the body surface can be minimized, and the catheter can be inserted smoothly into the body. When the catheter is inserted into the body, the body part of the auxiliary dilator is removed from the main dilator by using the separation part. It is thus possible to perform a desired operation by using the main dilator and the catheter similarly to the conventional catheter assembly after forming a hole of a sufficient size in the body surface. It is therefore possible to provide an auxiliary dilator having a simple structure that does not affect the operation after inserting the front end of the catheter into the body.

<2> In the second aspect of the present invention, the separation part of the auxiliary dilator has a pair of small pieces attached to the rear end portion of the body part of the auxiliary dilator. Therefore, an operator such as a physician can easily remove the auxiliary dilator from the main dilator by holding the small pieces and splitting the body part in the axial direction.

<3> The catheter assembly according to the third aspect of the present invention includes the catheter, the main dilator, and the auxiliary dilator. By using the catheter assembly, it is possible to realize a minimally invasive operation that allows the hole formed in the body surface to have a minimum size and the catheter to be smoothly inserted into the body.

<4> In the fourth aspect of the present invention, the taper angle of the front end portion of the extension part of the main dilator and the taper angle of the tapered portion of the auxiliary dilator are substantially equal to each other. In addition, when the auxiliary dilator is fitted to the main dilator, the tapered inclined surface of the front end portion of the extension part of the main dilator and the tapered inclined surface of the tapered portion of the auxiliary dilator are substantially in alignment with each other. Such a configuration allows the tapered portion of the auxiliary dilator to smoothly enter the body after the front end portion of the main dilator enters the body.

A catheter assembly according to a first embodiment will be described with reference to FIGS. 1 to 6C.

In FIGS. 1 to 6C, the left side shown is the front side (distal side) of the catheter assembly to be inserted into a body, and the right side is the rear side (proximal side, base end side) of the catheter assembly to be operated by an operator such as a physician.

The entire length of a catheter assembly 10 according to the present embodiment is about 800 mm to about 1500 mm.

Figure 2:
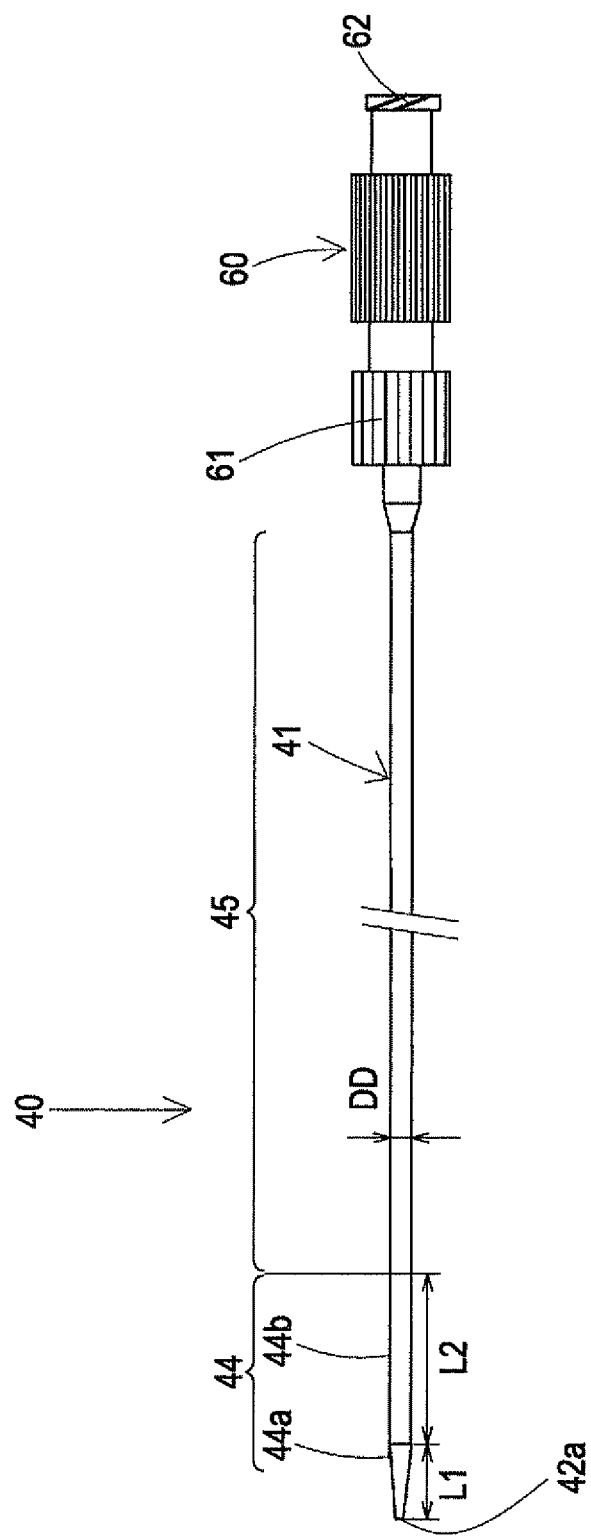
FIG. 2 is a view illustrating an entire main dilator of the catheter assembly according to the first embodiment.
Figure 3:
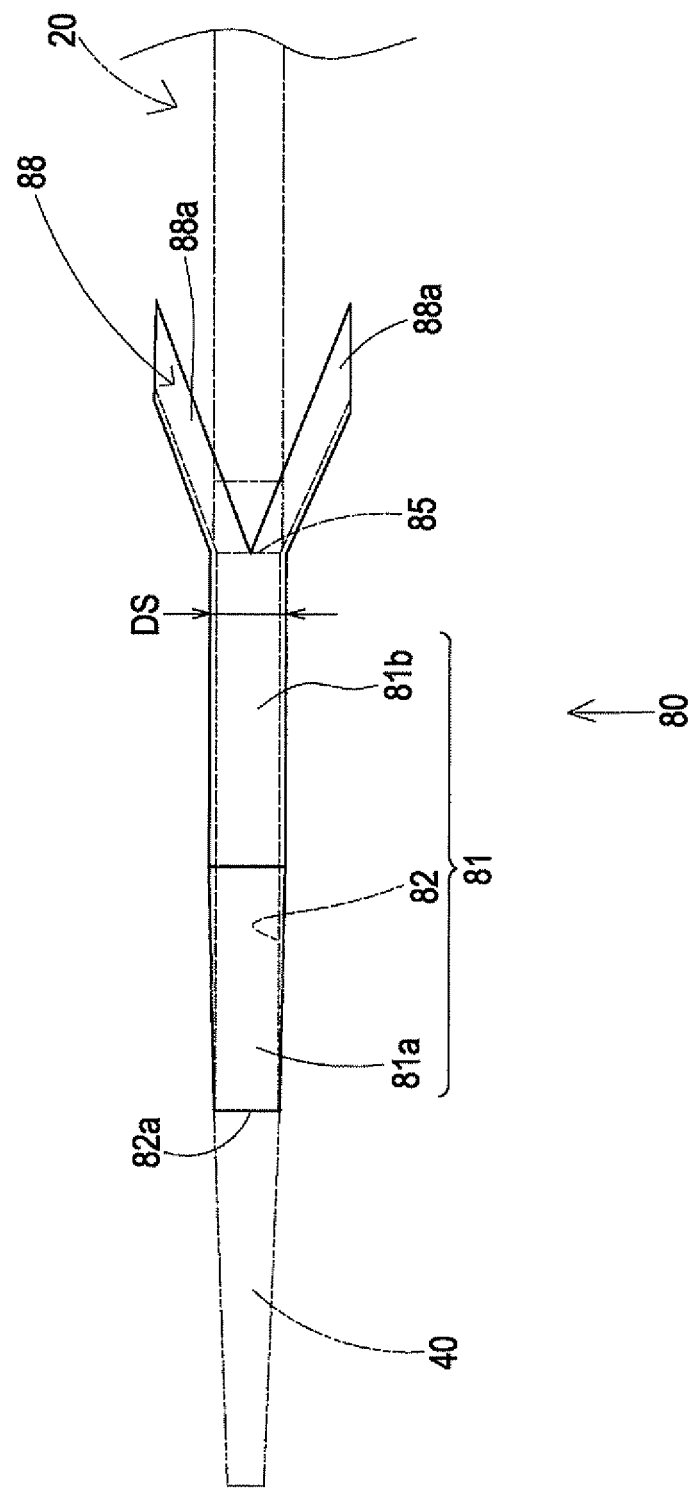
FIG. 3 is a view illustrating an entire auxiliary dilator of the catheter assembly according to the first embodiment.
Figure 4:
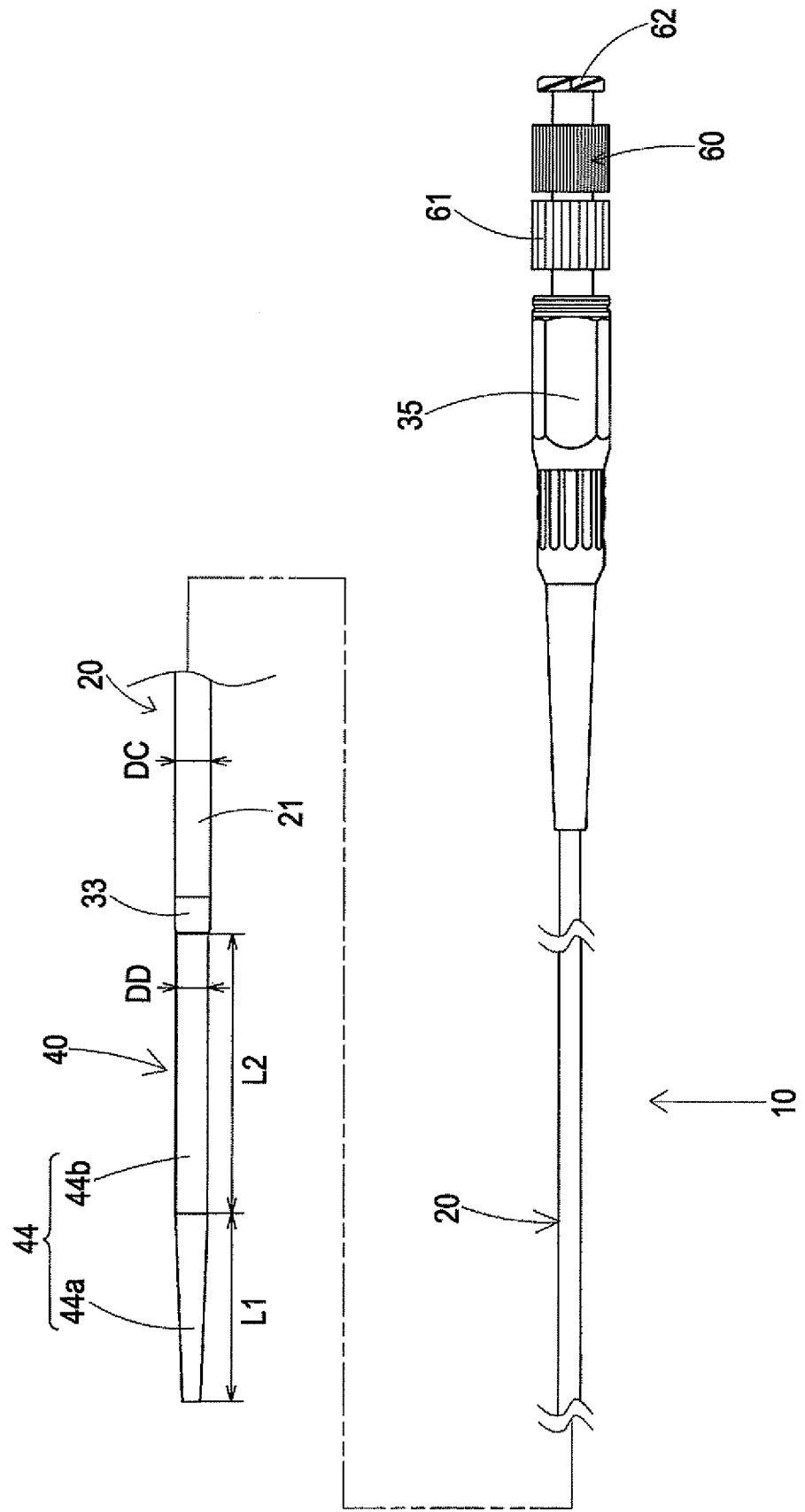
FIG. 4 is a view illustrating the catheter assembly according to the first embodiment in which the main dilator is fitted to the catheter.
Figure 5:
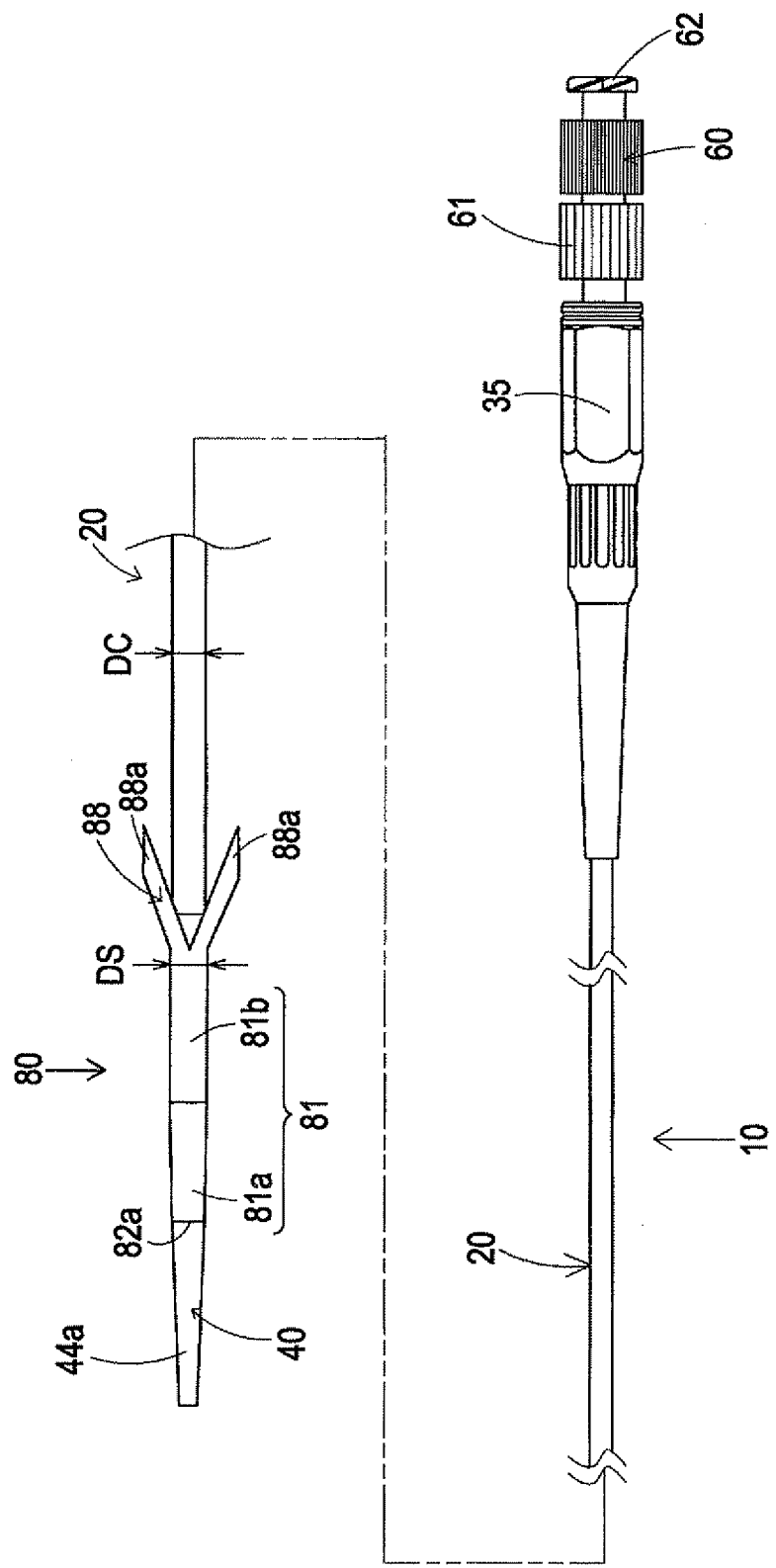
FIG. 5 is a view illustrating the catheter assembly according to the first embodiment in which the main dilator is fitted to the catheter and the auxiliary dilator is fitted to the main dilator.

The catheter assembly 10 includes a catheter 20, a main dilator 40 and an auxiliary dilator 80 as illustrated in FIG. 5. FIGS. 1, 2 and 3 illustrate the catheter 20, the main dilator 40 and the auxiliary dilator 80, respectively. FIG. 4 illustrates a state in which the main dilator 40 is inserted into the catheter 20. FIG. 5 illustrates a state in which the main dilator 40 is inserted into the catheter 20 and the auxiliary dilator 80 is fitted to a front end portion of the main dilator 40. Note that FIGS. 4 and 5 illustrate a state in which a curved portion 28 at the front side of the catheter 20 is unbent linearly for easy understanding. In addition, a curved portion 30 at the rear side is not illustrated. FIGS. 6A, 6B and 6C illustrate a positional relationship between structural elements of the catheter 20, the main dilator 40 and the auxiliary dilator 80 assembled as illustrated in FIG. 5. For easy understanding, the curved portion 28 at the front side of the catheter 20 is also illustrated in the linearly unbent state in FIG. 6A. Also for easy understanding, dimensions of some structural elements are illustrated in an exaggerated manner.

The illustrated catheter 20 is a catheter for diagnosis. In the first embodiment, the catheter 20 is used, for example, as a guiding catheter for guiding a balloon catheter or the like for treating a stenosis of a vessel in the heart or the like. More specifically, the catheter 20 illustrated in FIG. 1 is typically a Judkins left coronary catheter. However, the catheter 20 is not limited to the Judkins left coronary catheter. The catheter 20 may have various curved shapes like a Judkins right coronary catheter or an Amplatz left or right coronary catheter. In addition, the catheter 20 may be linear but is not particularly limited to the linear shape.

The catheter 20 mainly includes a catheter shaft 21, a tip 33 and a connector 35.

The catheter shaft 21 is a circular in its cross section and tubular member having a lumen 22 therein. As illustrated in FIG. 6A, the catheter shaft 21 has an inner layer 23 made of resin and forming the lumen 22, a braid 24 arranged on the outer surface of the inner layer 23 and an outer layer 25 made of resin coating the outer surface of the braid 24. Examples of the resin material of the inner layer and the outer layer of the catheter shaft 21 include polyamide, polyester and polyurethane. The braid 24 has a known configuration in which metal wires such as stainless steel wires are wound in the form of mesh.

As described above, the catheter shaft 21 of the Judkins left coronary catheter 20 according to the first embodiment has two curved portions. Therefore, the catheter shaft 21 has a first straight shaft portion 27, a first curved portion 28, a second straight shaft portion 29, a second curved portion 30, and a body shaft portion 31 in this order from the front end thereof.

The first straight shaft portion 27 is a straight portion arranged on the rear side of the tip 33 described later.

The first curved portion 28 on the front side is arranged on the rear side of the first straight shaft portion 27. FIG. 1 illustrates a curving range C1 of the first curved portion 28. The rear end of the range C1 is set, for example, within about 30 mm of the front end of the catheter 20. When the main dilator 40 is not inserted into the catheter 20, the catheter shaft 21 is curved at about 90 degrees at the first curved portion 28.

The second straight shaft portion 29 is a straight portion arranged on the rear side of the first curved portion 28.

The second curved portion 30 is arranged on the rear side of the second straight shaft portion 29. FIG. 1 illustrates a curving range C2 of the second curved portion 30. When the main dilator 40 is not inserted into the catheter 20, the catheter shaft 21 is curved at about 180 degrees at the second curved portion 30.

The body shaft portion 31 is a substantially straight portion forming the rest of the catheter shaft 21 on the rear side of the second curved portion 30.

The tip 33 is attached to the front end of the first straight shaft portion 27 of the catheter shaft 21. The tip 33 is a cylindrical member forms an open front end portion of the lumen 22 so as to have an opening 22a of the lumen 22 at the front end of the tip 33. The axial length of the tip 33 is about 3.0 mm. In the first embodiment, the front end portion of the catheter shaft 21 connected to the tip 33 has an outer diameter DC of about 2.8 mm.

The resin material of the tip 33 is similar to that of the catheter shaft 21. However, the resin material of the tip 33 is typically softer than that of the catheter shaft 21. In addition, the resin material of the tip 33 contains a radiopaque material so as to locate the catheter 20 under radioscopy.

The tip 33 has, at the front end thereof, a tapered portion 33a tapering toward the front end. The tapered portion 33a allows a stepped portion, which will be described later, between the front end of the tip 33 and an extension part 44 of the main dilator 40 as small as possible. The tapered portion 33a is designed to contact a connecting portion 85 of the auxiliary dilator 80.

Note that the outer surface of the catheter shaft 21 of the catheter 20 and the outer surface of the tip 33 are provided with hydrophilic coating.

The connector 35 is attached to the rear end of the catheter shaft 21. The connector 35 has therein a hollow portion communicating with the lumen 22 of the catheter shaft 21. A threaded portion 36 is provided at the rear end of the connector 35. The threaded portion 36 is threadably engaged with a rotational portion 61 of a connector 60 of the main dilator 40 described later.

The main dilator 40 is a cylindrical member having a lumen 42 therein and a front end entry portion 44a that is a tapered front end portion. The main dilator 40 mainly includes a main dilator shaft 41 and the connector 60. As illustrated in FIG. 4, the entire main dilator 40 is set longer than the entire catheter 20 by a predetermined length. With this configuration, the front end of the main dilator 40 protrudes from the front end of the catheter 20 when the main dilator 40 is inserted into the catheter 20 and the connector 60 of the main dilator 40 is connected to the connector 35 of the catheter 20 (hereinafter expressed as "when the main dilator is attached to the catheter").

The main dilator shaft 41 is made of a single resin material. Examples of the resin material include fluorine resin such as PTFE, polyamide, polyester and polyethylene. The main dilator shaft 41 has a front end portion that is first to enter the body when the catheter assembly is inserted into the body. Therefore, the main dilator shaft 41 is typically made of a resin material that is harder than those of the catheter shaft 21 and the tip 33.

The main dilator shaft 41 has two structural parts: a first structural part corresponds to the extension part 44 that extends from the front end of the catheter 20 when the main dilator 40 is attached to the catheter 20; and a second structural part corresponds to an inserted part 45 inside the catheter 20 when the main dilator 40 is attached to the catheter 20. The extension part 44 includes the aforementioned front end entry portion 44a. Specifically, the extension part 44 includes the front end entry portion 44a and a straight portion 44b provided on the rear side of the front end entry portion 44a. The straight portion 44b is a cylindrical portion having an outer diameter equal to that of the inserted part 45. The outer diameter DD of a part including the straight portion 44b and the inserted part 45 is set to about 2.2 mm in the first embodiment.

The front end entry portion 44a of the extension part 44 is tapered. Herein, "tapered" refers to a state in which the peripheral surface of the front end entry portion 44a is inclined in the axial direction so that the outer diameter thereof decreases from the rear end of the front end entry portion 44a toward the front end thereof to form an inclined surface at a predetermined inclination angle (taper angle) with respect to the central axis of the front end entry portion 44a. The front end entry portion 44a has an opening 42a of the lumen 42 formed at the front end thereof. With this configuration, the front end entry portion 44a facilitates entry of the catheter assembly 10 into the body. The axial length L1 of the front end entry portion 44a is set to about 12 mm to about 25 mm. In the first embodiment, the axial length L1 is set to about 15 mm, for example.

The straight portion 44b is a cylindrical portion having a constant outer diameter. The straight portion 44b is a portion to which the auxiliary dilator 80 is attached. The axial length L2 of the straight portion 44b is set to about 40 mm to about 52 mm.

The inserted part 45 is continuous to the straight portion 44b and constitutes the rest of the main dilator shaft 41.

The connector 60 has therein a hollow portion communicating with the lumen 42 of the main dilator shaft 41. A rotational portion 61 that is threadably engaged with the threaded portion 36 of the connector 35 of the catheter 20 is provided at the front end of the connector 60. The connector 60 also has, at the rear end thereof, a rear end opening 62 through which a guidewire (not illustrated) inserted into the lumen 42 extends.

When the main dilator 40 is attached to the catheter 20 configured as described above, the extension part 44 of the main dilator 40 extends outward from the front end of the catheter 20. Specifically, the front end entry portion 44a and the straight portion 44b are exposed outside through the front end of the catheter 20.

The auxiliary dilator 80 is a cylindrical member having therein a lumen 82 into which the extension part 44 of the main dilator 40 is inserted. The auxiliary dilator 80 mainly has a body part 81 and a separation part 88. The body part 81 has a tapered portion 81a on the front side and a cylindrical portion 81b on the rear side. The separation part 88 is provided at the rear end of the cylindrical portion 81b of the body part 81. The lumen 82 is formed in the body part 81 along the axial direction. The inner diameter of the lumen 82 is set to be as small as possible within a range in which the straight portion 44b of the extension part 44 can be fitted into the lumen 82 when the main dilator 40 is inserted through the lumen 82. Specifically, the inner diameter of the lumen 82 is slightly larger than the outer diameter DD of the straight portion 44h of the main dilator shaft 41. Thus, as will be described later, a rear end portion of the lumen 82 is connected as the connecting portion 85 to the tapered portion 33a of the tip 33 of the catheter 20. On the other hand, the inner diameter of the lumen 82 is not large enough for the front end portions of the tip 33 and the catheter shaft 21 to be inserted into the lumen 82.

The auxiliary dilator 80 is made of a single resin material. The resin material may be similar to that of the main dilator 40. Specifically, examples of the material used therefor include fluorine resin (such as PET), polyamide, polyester and polyethylene. The auxiliary dilator 80 includes a front end portion that is also enter the body before the catheter 20 enters the body similarly to the main dilator 40. Accordingly, the auxiliary dilator 80 is typically made of a resin that is harder than those of the catheter shaft 21 and the tip 33.

When the main dilator 40 is attached to the catheter 20 and the auxiliary dilator 80 is fitted to the straight portion 44b of the main dilator 40 (hereinafter expressed as "when the auxiliary dilator is attached to the main dilator"), a rear end of the cylindrical portion 81b of the auxiliary dilator 80 is in contact with the front end of the catheter 20. In this state, the front end entry portion 44a of the main dilator 40 protrudes from the front end of the tapered portion 81a. Specifically, the axial length of the body part 81 of the auxiliary dilator 80 is set to be substantially equal to the axial length L2 of the straight portion 44b of the main dilator 40.

The peripheral surface of the tapered portion 81a is inclined in the axial direction. Thus, the outer diameter of the tapered portion 81a decreases toward the front end. An opening 82a of the lumen 82 is formed at the front end of the tapered portion 81a. The tapered portion 81a has an inclination angle (taper angle) substantially equal to that of the front end entry portion 44a of the main dilator 40. With this configuration, when the auxiliary dilator 80 is attached to the main dilator 40, the inclined surface of the front end entry portion 44a of the main dilator 40 and the inclined surface of the tapered portion 81a of the auxiliary dilator 80 are substantially in alignment with each other as illustrated in FIGS. 3 and 5. Therefore, the tapered portion 81a of the auxiliary dilator 80 smoothly enters the body following the front end entry portion 44a of the main dilator 40 entering the body.

The cylindrical portion 81b is a portion formed on the rear side of the tapered portion 81a integrally therewith and having a constant outer diameter. The outer diameter DS of the cylindrical portion 81b is substantially equal to the outer diameter DC of the front end portion of the catheter shaft 21. In the first embodiment, the outer diameter DC of the front end portion of the catheter shaft 21 is about 2.8 mm as described above. Accordingly, the outer diameter DS of the cylindrical portion 81b is about 2.7 mm to about 2.85 mm.

Note that the outer diameter DS of the cylindrical portion 81b can be set to be sufficiently larger than the outer diameter of the catheter shaft 21. This setting is preferable for insertion of the catheter 20. However, if application of the catheter 20 to a thin artery such as a radial artery and the strain on a patient, for example, are considered, the hole bored in a vessel or the like is preferably as small as possible within a range in which the catheter 20 can be inserted. Therefore, in the first embodiment, the outer diameter DS of the cylindrical portion 81b is substantially equal to the outer diameter DC of the front end portion of the catheter shaft 21.

The cylindrical portion 81b is provided with the separation part 88 on the rear side thereof. The separation part 88 is formed by splitting the resin tube forming the body part 81 to branch into two small pieces 88a. Thus, the auxiliary dilator 80 is removed from the main dilator 40 in the following manner. First, an operator such as a physician holds the small pieces 88a. Next, the operator splits the auxiliary dilator 80 from the cylindrical portion 81b toward the tapered portion 81a. As a result, the auxiliary dilator 80 is removed from the main dilator 40. The length of the small pieces 88a is not particularly limited as long as the small pieces 88a can be held by finger tips. For example, the small pieces 88a have a length of about 10 mm to 30 mm.

The rear end portion of the cylindrical portion 81b that is a branching point of the small pieces 88a is the connecting portion 85 that comes in contact with the front end of the tip 33 that is the front end portion of the catheter 20. That is, the connecting portion 85 is the branching point of separation of the separation part 88, which is divided into two small pieces 88a and widened. Accordingly, the inner diameter of the cylindrical portion 81b becomes slightly larger at this branching point. It is thus possible to insert the tapered portion 33a of the tip 33 of the catheter 20 through the connecting portion 85 in contact with each other.

When the main dilator 40 is attached to the catheter 20 having the above-described configuration, the extension part 44 of the main dilator 40 protrudes from the front end of the catheter 20 as illustrated in FIG. 4. When the auxiliary dilator 80 is attached to the main dilator 40 in this state, the auxiliary dilator 80 is fitted to the straight portion 44b of the extension part 44 as illustrated in FIG. 5 so that the front end entry portion 44a of the extension part 44 protrudes from the front end of the auxiliary dilator 80. At this point, the inclined surface of the front end entry portion 44a of the main dilator 40 and the inclined surface of the tapered portion 81a of the auxiliary dilator 80 are substantially in alignment with each other.

Next, insertion of the catheter assembly 10 having the above-described configuration according to the first embodiment into an aorta in the heart will be described with reference to FIGS. 7A to 7C, 8A and 8B. Note that one example of the catheter 20 according to the first embodiment is the Judkins left coronary catheter as described above. In the following description, therefore, the catheter 20 is to be engaged with a left coronary artery.

The catheter assembly 10 before being inserted into the body is in a state in which the auxiliary dilator 80 is attached to the main dilator 40 after the main dilator 40 is attached to the catheter 20 as illustrated in FIG. 5. The catheter assembly 10 in this state is inserted through a radial artery in a wrist region. The auxiliary dilator 80 is removed before the catheter 20 is inserted into the body. That is, only the catheter 20 and the main dilator 40 are inserted into the aorta through vessels in the vicinity of an upper arm and a collarbone. The main dilator 40 is also removed thereafter. As a result, only the catheter 20 is engaged with the left coronary artery ostium. A treatment catheter (not illustrated) or the like such as a balloon catheter is inserted through the lumen 22 of the catheter 20 in this state. This treatment catheter or the like is used to treat a stenosis inside a coronary artery or the like.

To perform such an operation, first, a minute hole is bored in the body surface 91 in a wrist region into the radial artery 90 with a puncture needle (not illustrated). Specifically, the puncture needle typically has an outer cylinder into which the guidewire GW is inserted, and an inner cylinder inserted into the outer cylinder and provided with a needle for puncture. The puncture needle with the inner cylinder inserted into the outer cylinder punctures through the body surface 91 in the wrist region into the radial artery 90. A minute hole 92a is thus bored in the artery 90. After that, only the inner cylinder is removed from the hole 92a. The hole 92a generally has such a size that the front end of the front end entry portion 44a at the extension part 44 of the main dilator 40 can be inserted into the hole 92a.

Figure 7A:
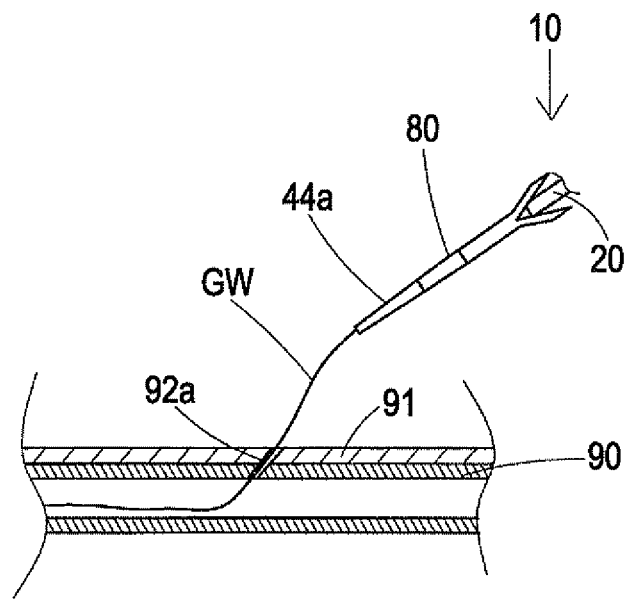
FIGS. 7A, 7B and 7C are explanatory drawings each illustrating function of the catheter assembly according to the first embodiment.

The guidewire GW (not illustrated) is inserted into the remaining outer cylinder. At this time, the guidewire GW is inserted up to the vicinity of the upper arm. Then, the outer cylinder of the puncture needle is removed. As a result, the rear side of the guidewire GW is exposed outside the body and the front side thereof remains in the artery 90 (FIG. 7A).

The catheter assembly 10 is inserted into the artery 90 through the rear end of the guidewire GW and along the guidewire GW in this state. Specifically, the rear end of the guidewire GW is inserted through the opening 42a formed at the front end of the front end entry portion 44a at the extension part 44 of the main dilator 40, passes through the lumen 42 of the main dilator 40 and extends through the rear end opening 62 of the connector 60. From this state, the catheter assembly 10 is made to enter the hole 92a formed in the body surface 91 into the body along the guidewire GW (FIG. 7A).

Figure 7B:
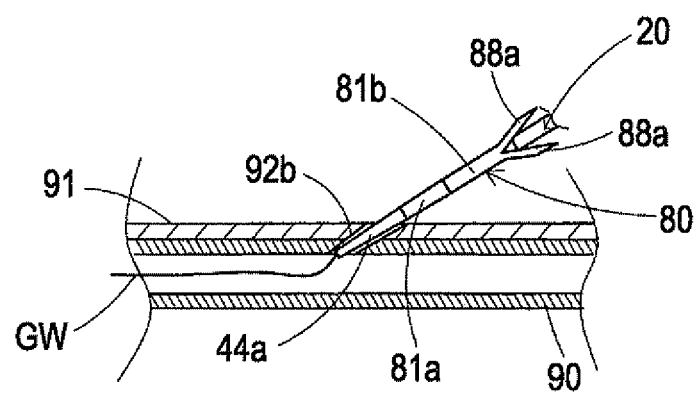

First, the front end entry portion 44a of the main dilator 40 enters the hole 92a formed in the body surface 91. The front end of the front end entry portion 44a of the extension part 44 is formed to have an outer diameter that becomes as small as possible. Accordingly, a stepped portion produced between the front end of the front end entry portion 44a and the surface of the guidewire GW becomes as small as possible. The front end entry portion 44a can therefore be guided by the guidewire GW and smoothly enter the body (FIG. 7B). At this time, the hole 92a is enlarged by the front end entry portion 44a. Herein, the enlarged hole 92a is referred to as a hole 92b. Since the diameter of the hole 92b is smaller than the outer diameter DC of the catheter 20, the hole 92b is not sufficiently large for the catheter 20 to enter the body.

Figure 7C:
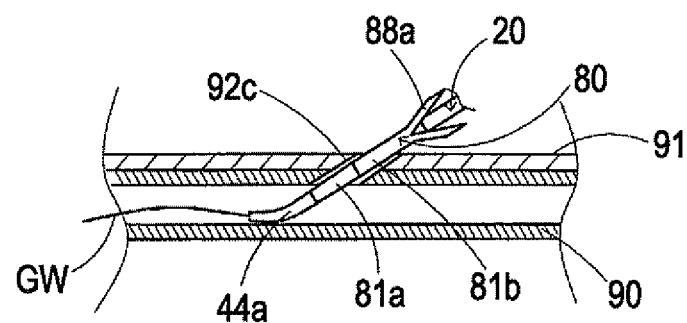

Next, the tapered portion 81a of the auxiliary dilator 80 enters the hole 92b formed in the body surface 91. At this time, the peripheral surface of the tapered portion 81a forms an inclined surface substantially in alignment with the front end entry portion 44a of the main dilator 40 along the axial direction. The tapered portion 81a can therefore smoothly enter the body (FIG. 7C). In this manner, the tapered portion 81a and the cylindrical portion 81b of the auxiliary dilator 80 further enlarge the hole 92b (hereinafter referred to as a hole 92c). The outer diameter DS of the cylindrical portion 81b is substantially equal to the outer diameter DC of the catheter 20. Thus, the hole 92c has a diameter substantially equal to the outer diameter DC of the catheter 20, which is a sufficient size for the catheter 20 to enter the body.

Figure 8A:
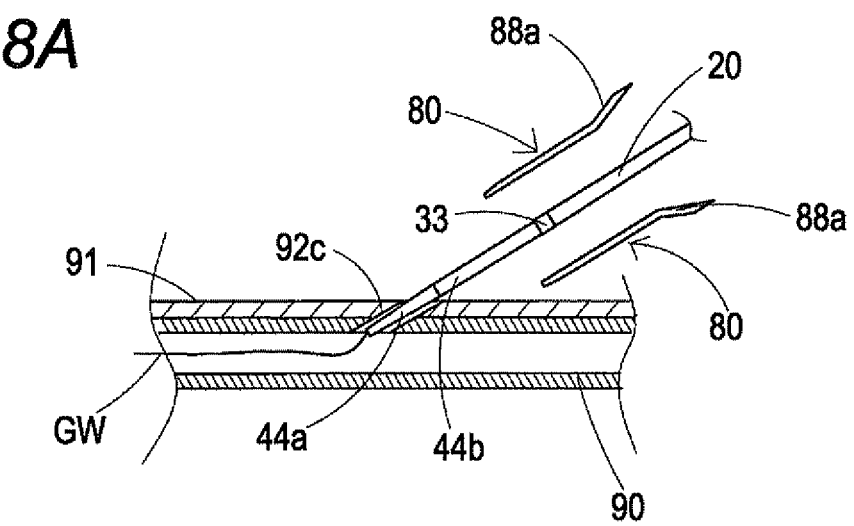
FIGS. 8A and 8B are explanatory drawings illustrating the function of the catheter assembly according to the first embodiment following FIGS. 7A, 7B, and 7C.

After the hole 92c is formed, the catheter assembly 10 is slightly moved backward along the guidewire GW. As a result, the auxiliary dilator 80 is exposed outside the body. The distance by which the catheter assembly 10 is moved backward is a distance that is sufficient to expose the entire catheter assembly 10 outside the body. Alternatively, the distance may be such that the front end entry portion 44a of the main dilator 40 remains in the body while the auxiliary dilator 80 is exposed outside the body. From this state, the operator such as a physician splits the auxiliary dilator 80 in the axial direction using the separation part 88 of the auxiliary dilator 80 to form two small pieces 88a. Then, the operator removes the auxiliary dilator 80 from the main dilator 40. This operation can be easily performed by holding the pair of small pieces 88a formed in the separation part 88 and pulling apart the pair of small pieces 88a in the radial direction of the auxiliary dilator 80 (FIG. 8A). As a result of this operation, only the catheter 20 and the main dilator 40 remain among the structural elements of the catheter assembly 10.

Figure 8B:
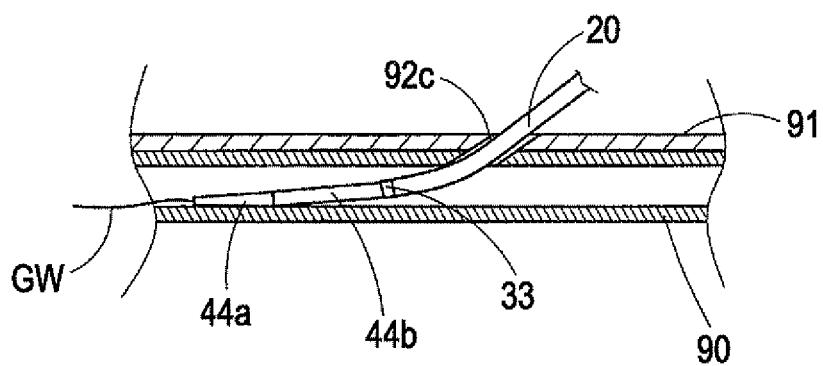

Next, the catheter assembly 10 is made to enter the body along the guidewire GW. The front end portion of the catheter 20 enters the body following the extension part 44 of the main dilator 40. At this time, since the diameter of the hole 92c formed in the body surface 91 is substantially equal to the outer diameter DC of the catheter 20, the catheter 20 can smoothly enter the body with the tip 33 at the leading end of the catheter 20 (FIG. 8B). Since the front end of the tip 33 of the catheter 20 is provided with the tapered portion 33a, the front end of the tip 33 of the catheter 20 and the extension part 44 of the main dilator 40 are smoothly connected. Therefore, the tip 33 of the catheter 20 can easily be made to enter the body.

After the tip 33 of the catheter 20 is inserted into the body, the first straight shaft portion 27, the first curved portion 28, the second straight shaft portion 29, the second curved portion 30 and the body shaft portion 31 are sequentially inserted into the body.

When the front end of the catheter assembly 10 approaches the front end of the guidewire GW in the upper arm, the operator such as a physician moves the guidewire GW and the catheter assembly 10 at the same time. With this operation, the catheter assembly 10, with a predetermined length of the guidewire GW protruding from the front end of the catheter assembly 10, passes through a vessel in the vicinity of the collarbone and reaches the vicinity of an inlet of an ascending aorta.

After that, the main dilator 40 is pulled out of the catheter 20 and then out of the body. The operator then makes the guidewire GW and the catheter 20 further advance toward the ascending aorta by operating the guidewire GW and the catheter 20. Then, the operator also removes the guidewire GW out of the body, and engages the front end of the catheter 20 with the left coronary artery ostium.

Note that the timing of removing the main dilator 40 and the guidewire GW depends on the operator, and is not limited to the above example.

When the catheter 20 is engaged with the coronary artery ostium in this manner, another guidewire or balloon catheter or the like is inserted into the catheter 20 to treat a target site, i.e., a stenosis inside the coronary artery or the like.

In the embodiment described above, the inclination angle (taper angle) in the axial direction of the tapered portion 81a of the auxiliary dilator 80 is substantially equal to the inclination angle (taper angle) in the axial direction of the front end entry portion 44a of the main dilator 40. However, these taper angles may be different from each other.

Figure 9:
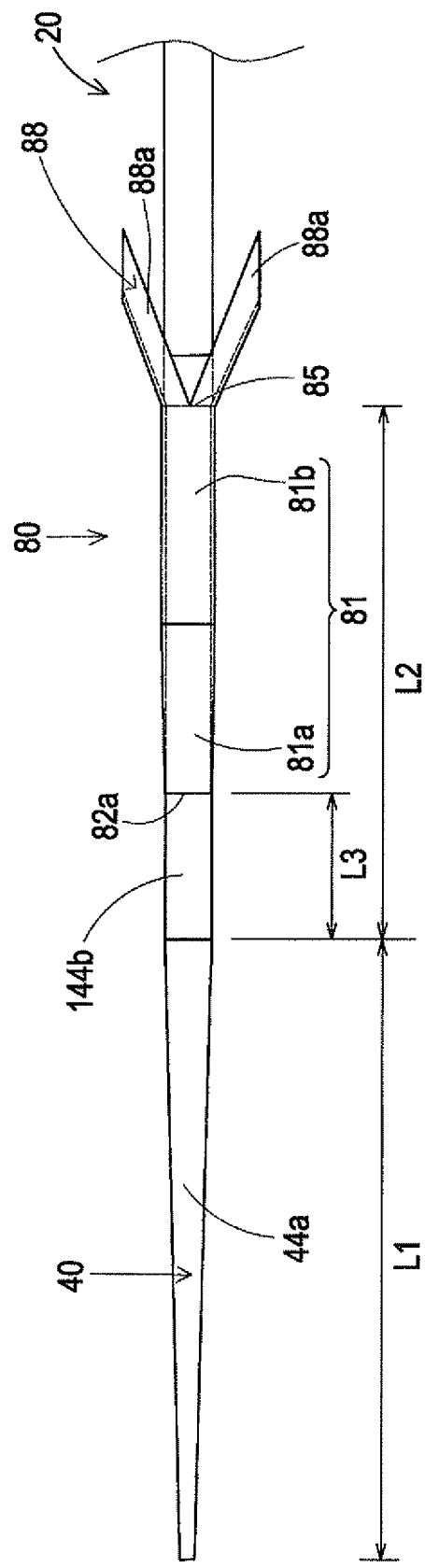
FIG. 9 is a view illustrating a catheter assembly according to a second embodiment.

In addition, in the embodiment described above, the sum of the axial length of the tapered portion 81a of the auxiliary dilator 80 and the axial length of the cylindrical portion 81b is substantially equal to the axial length L2 of the straight portion 44b of the main dilator 40. Furthermore, the inclined surface in the axial direction of the front end entry portion 44a of the main dilator 40 and the inclined surface in the axial direction of the tapered portion 81a of the auxiliary dilator 80 are in alignment with each other. Alternatively, like a catheter assembly illustrated in FIG. 9 (second embodiment), the axial length L2 of the straight portion 44b of the main dilator 40 may be longer by a distance L3 relative to the axial length of the body part 81 of the auxiliary dilator 80. With this configuration, a portion 144b having a constant outer diameter is formed between the front end entry portion 44a of the main dilator 40 and the tapered portion 81a of the auxiliary dilator 80.

In the embodiments described above, the catheter 20 of the catheter assembly 10 is a guiding catheter for the heart. However, the catheter 20 of the catheter assembly 10 is not limited thereto and can be applied to other catheters.

In addition, the organ for which the catheter 20 is used is not limited to a vessel in the heart. The catheter 20 can be used in an operation for other organs.

While the invention has been shown and described in detail, the foregoing description is in all aspects illustrative and not restrictive. It is therefore understood that numerous modifications and variations can be devised without departing from the spirit and scope of the invention.

The invention claimed is:

1. A catheter assembly comprising:
    a catheter having a catheter shaft and a tip attached to a front end of the catheter shaft;
    a main dilator to be inserted into the catheter, the main dilator having an extension part that extends from a front end of the tip of the catheter; and
    an auxiliary dilator configured to be attached to the main dilator, the auxiliary dilator comprising:
        a lumen formed along an axial direction of the auxiliary dilator;
        a body part having a tapered portion tapering towards a front end of the auxiliary dilator, and a cylindrical portion that is formed on a rear side of the tapered portion;
        a separation part attached to a rear end of the body part, the separation part branching into two small pieces and widening; and
        a connecting portion that is a branching point of the separation part; wherein
            an inner diameter of the cylindrical portion becomes slightly larger at the branching point;
            the front end of the tip of the catheter is in contact with the rear end of the body part when the auxiliary dilator, the catheter, and the main dilator are assembled; and
            the cylindrical portion of the auxiliary dilator has an outer diameter that is larger than an outer diameter of the catheter shaft.

2. The catheter assembly according to claim 1, wherein the lumen has an inner diameter that is smaller than the outer diameter of the catheter shaft.

* * * * *